US00PP31382P2

(12) United States Plant Patent
Keysers

(10) Patent No.: US PP31,382 P2
(45) Date of Patent: Jan. 21, 2020

(54) ***ABELIA* PLANT NAMED 'LADY PEACH'**

(50) Latin Name: *Abelia grandiflora*
Varietal Denomination: LADY PEACH

(71) Applicant: Klemens Keysers, Kevelaer (DE)

(72) Inventor: Klemens Keysers, Kevelaer (DE)

( * ) Notice: Subject to any disclaimer, the term of this patent is extended or adjusted under 35 U.S.C. 154(b) by 0 days.

(21) Appl. No.: 15/999,875

(22) Filed: Aug. 23, 2018

(51) Int. Cl.
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

(56) References Cited

PUBLICATIONS

UPOV Record Detail Feb. 15, 2017.*

* cited by examiner

*Primary Examiner* — Keith O. Robinson
(74) *Attorney, Agent, or Firm* — Cassandra Bright

(57) ABSTRACT

A new and distinct *Abelia* cultivar named 'LADY PEACH' is disclosed, characterized by green foliage with cream-colored variegation. Plants are moderately compact and well suited for use in containers. The new variety is a *Abelia*, normally produced as an outdoor garden or good container plant.

1 Drawing Sheet

Latin name of the genus and species: *Abelia grandiflora*.
Variety denomination: 'LADY PEACH'.

BACKGROUND OF THE INVENTION

The new *Abelia* cultivar is a product of a chance discovery by the inventor in Kevelaer, Germany. The new variety was discovered as a naturally occurring single branch mutation in August of 2015.

The parent is *Abelia grandiflora* 'Lady Surnmerdream', unpatented.

Asexual reproduction of the new cultivar 'LADY PEACH' was first performed in September of 2015 at a nursery in Kevelaer, Germany. Vegetative soft wood cuttings were used. Subsequently, 3 generations have been reproduced and shown that the unique features of this cultivar are stable and reproduced true to type.

SUMMARY OF THE INVENTION

The cultivar 'LADY PEACH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LADY PEACH'. These characteristics in combination distinguish 'LADY PEACH' as a new and distinct *Abelia* cultivar:

1. Green foliage with cream variegation.
2. Good container plant.

PARENT COMPARISON

Plants of the new cultivar 'LADY PEACH' are similar to plants of the parent variety in most horticultural characteristics, however, plants of the new cultivar 'LADY PEACH' differ in the following:

1. The new variety has foliage with a green center and a moderately and irregularly thick cream margin. The parent variety has foliage with a green center and yellow and orange margin.
2. Plants of the new variety are more compact than plants of the parent.

COMMERCIAL COMPARISON

Plants of the new cultivar 'LADY PEACH' can be compared to the variety *Abelia* 'Kaleidoscope' U.S. Plant Pat. No. 16,988. These varieties are similar in most horticultural characteristics however, 'LADY PEACH' differs in the following:

1. The new variety has cream and green variegation. This comparator has yellow and green variegation.
2. The new variety has larger flowers than this comparator.
3. The new variety's young leaves have orange variegation. This comparator's young leaves have a darker red variegation.

BRIEF DESCRIPTION OF THE PHOTOGRAPH

The accompanying photograph illustrates in full color a typical plant of 'LADY PEACH' grown in 1 gallon container, at approximately 1 year old, The plant was grown in a polyhouse in Grand Haven, Mich. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, $6^{th}$ edition, except where general terms of ordinary dictionary significance are used. The following observations and measurements describe 'LADY PEACH' plants grown in a polyhouse in Grand Haven, Mich. Measurements were taken during May. The plants were about 2 years old in 5 gallon containers. The growing temperature ranged from approximately 18° C. to 27° C. during the day and 5° C. to 10° C. at night. Measurements and numerical values represent averages of typical plant types.

Botanical classification: *Abelia grandiflora* 'LADY PEACH'.

PROPAGATION

Time to initiate roots: 1 to 2 months at approximately 18 to 27° C.

Root description: Fibrous, fleshy, thin. Moderate density, freely branching. Tan and white in color, not effectively measured with a color chart.

Time to produce a rooted young plant: About 40 days at approximately 18 to 27° C.

PLANT

Plant type: Perennial flowering shrub.
Age of plant described: Approximately 2 to 3 years old.
Growth habit: Outward.
Growth rate: Moderate.
Pot size of plant described: 1-gallon pot.
Overall plant shape: Outward, flattened oval.
Height: 12 cm.
Plant spread: 18 cm.
Plant vigor: Good.
Branching characteristics: Basal and lateral branching. Pinching required.
Length of primary lateral branches: 9 cm.
Diameter of lateral branches: 2 mm.
Quantity of lateral branches: 5.
Stem:
- *Stem shape*.—Round.
- *Stem strength*.—Flexible.
- *Color*.—Greyed-Red 182A.
- *Texture*.—Slightly pubescent.
- *Angle of attachment*.—45 degrees.

Internode length: 1 cm.
- *Anthocyanin coloration*.—Very strong.

FOLIAGE

Leaf:
- *Arrangement*.—Opposite.
- *Leaf shape*.—Lanceolate.
- *Average length*.—2 cm.
- *Average width*.—1.25 cm.
- *Apex*.—Acute or acuminate.
- *Base*.—Obtuse.
- *Margin*.—Crenate.
- *Texture of top surface*.—Waxy.
- *Texture of bottom surface*.—Waxy, protruding midrib.
- *Color*.—Young foliage, upper side: Middle: Close to Grey-Brown N199A. Variegated Margin: Near Orange-Red 34C. Young foliage, under side: Middle: Close to Grey-brown N199A. Variegated Margin: Orange-Red 34C. Mature foliage upper side: Middle: Green 139B. Variegated Margin: Yellow 8B mixed with White 155A, creating a cream appearance. Mature foliage under side: Middle: Green 138A. Variegated Margin: Yellow 8B mixed with White 155A.
- *Venation*.—Pattern: Pinnate. Color upper side: Yellow 8B and White 155A. Color under side: Green 138A. Glossiness: Medium.
- *Petiole*.—Average Length: 2 mm. Diameter: 1 mm. Petiole color upper side: Green 138A with some Greyed-Red 179A on edges. Petiole color lower side: Green 138A with some Greyed-Red 178A on edges. Petiole Texture: Smooth, waxy.

FLOWER

Natural flowering season: Spring to Summer.
Flowering form: Single salverform flowers.
Quantity of flowers per flowering stem/inflorescence: About 15.
Quantity of flower buds per lateral stem: 5-10.
Inflorescence type: Axillary cyme.
Size:
- *Length*.—3.2 cm.
- *Diameter*.—1.5 cm.

Flower other characteristics:
- *Throat diameter*.—5 mm.
- *Flower tube length*.—7.5 mm.
- *Flower tube diameter*.—3 mm.
- *Aspect*.—Upwards, outwards, downwards.
- *Persistence*.—Self-cleaning.
- *Fragrance*.—Sweet.

Bud:
- *Shape*.—Linear-Spatulate.
- *Length*.—1 cm.
- *Diameter*.—1 cm.
- *Color*.—Red-purple 68B.

Petal:
- *Petal arrangement*.—Whorl, with a tubular base.
- *Number of petals per flower*.—5.
- *Petal shape*.—Elliptic to Obovate.
- *Petal base*.—Fused.
- *Margin*.—Entire.
- *Tip shape*.—Obtuse.
- *Unfused length*.—1 cm.
- *Unfused width*.—7.5 mm.
- *Tube length*.—About 2.5 cm.
- *Tube width*.—Widest point about 15 mm, narrowest point about 7 mm.
- *Texture*.—Upper: Smooth. Lower: Smooth.

Blotches in flower throat: Absent.
Color:
- *When opening*.—Upper side: Red-Purple 69C with slight Purple 75B. Under side: Red-Purple 69C with slight Purple 75B.
- *Fully opened*.—Upper side: Red-Purple 69C with slight Purple 75B. Under side: Red-Purple 69C with slight Purple 75B.
- *Flower tube*.—Red-Purple 69C with slight Purple 75B.
- *Flower throat*.—Red-Purple 69C with slight Purple 75B.

Sepal:
- *Arrangement*.—Whorl.
- *Number*.—5.
- *Shape*.—Elliptic.
- *Tip*.—Acute.
- *Base*.—Truncated.

*Margin*.—Entire.
*Length*.—7.5 mm.
*Width*.—3 mm.
*Texture, upper*.—Smooth.
*Texture, lower*.—Smooth.
*Color*.—Upper side: Red 51A. Under side: Red 51A.

Peduncle:
*Length*.—5 mm.
*Diameter*.—1 mm.
*Color*.—Green 143C.
*Orientation*.—45°.
*Strength*.—Good.
*Texture*.—Smooth.

REPRODUCTIVE ORGANS

Stamens:
*Number*.—4.
*Filament length*.—1 cm.
*Filament color*.—White N155D.

Anthers:
*Shape*.—Oblong.
*Length*.—2 mm.
*Color*.—White N155D.
*Pollen color*.—White N155D.
*Pollen amount*.—Minimal.

Pistil:
*Number*.—1.
*Length*.—1 cm.
*Style*.—Length: 1.5 cm. Color: White N155D.
*Stigma*.—Shape: Round. Color: Greyed green 197D.
*Position*.—Below anthers.

OTHER CHARACTERISTICS

Seeds and fruits: Not available at the time of filing.

Disease/pest resistance: Neither resistance nor susceptibility to normal diseases and pests of *Abelia grandiflora* have been observed.

Temperature tolerance: Typical range USDA zones 5 through 9.

What is claimed is:

1. A new and distinct cultivar of *Abelia* plant named 'LADY PEACH' as herein illustrated and described.

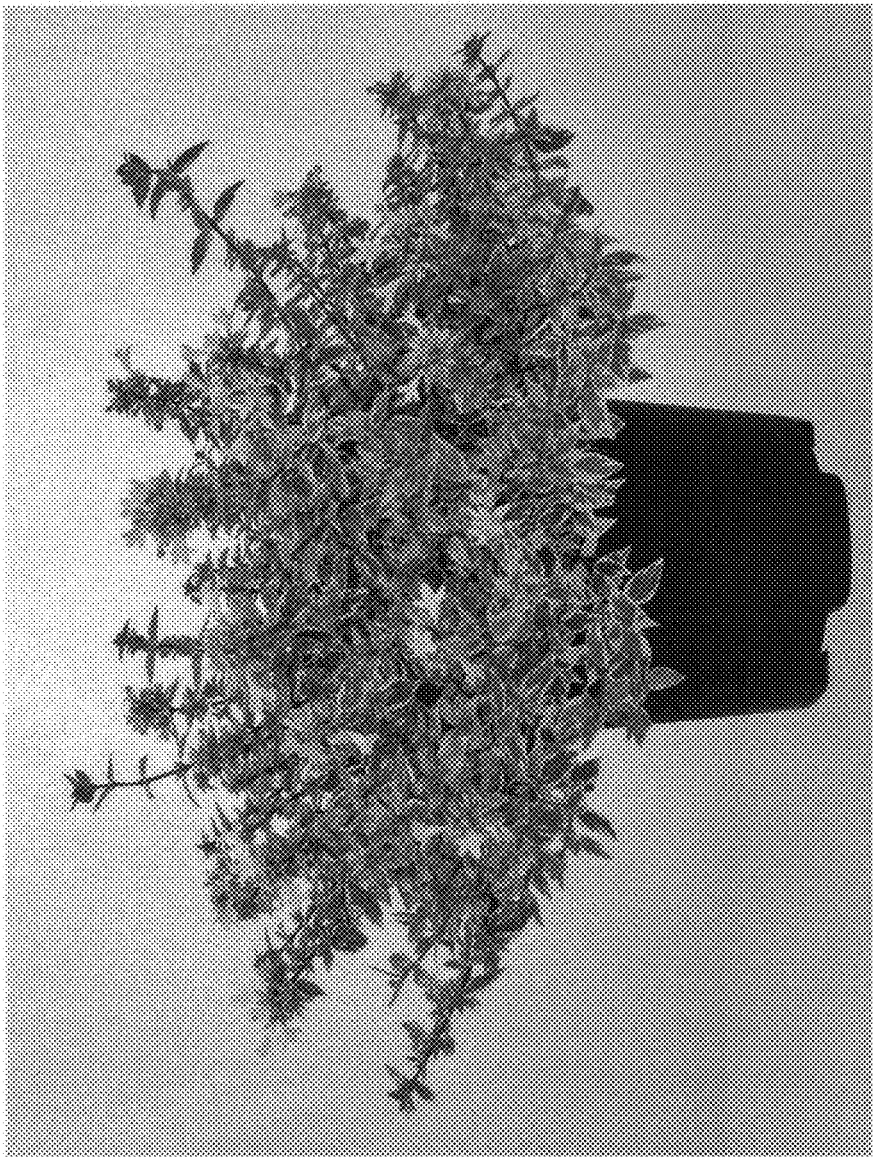

* * * * *